United States Patent [19]

Durant et al.

[11] 4,282,213
[45] Aug. 4, 1981

[54] AMIDINO AND GUANIDINO PHOSPHONATES

[75] Inventors: Graham J. Durant, Welwyn Garden City; Rodney C. Young, Bengeo, both of England; Zev Tashma, Jerusalem, Israel

[73] Assignee: Smith Kline & French Laboratories Limited, Welwyn Garden City, England

[21] Appl. No.: 70,208

[22] Filed: Aug. 27, 1979

Related U.S. Application Data

[62] Division of Ser. No. 913,180, Jun. 6, 1978, Pat. No. 4,190,664.

[51] Int. Cl.$^3$ .......................... C07F 9/58; C07F 9/65; A61K 31/675
[52] U.S. Cl. .................................... 424/200; 548/111; 548/119; 546/22; 546/24; 544/243
[58] Field of Search ...................... 548/111, 112, 119; 546/22, 24; 544/243; 424/200

[56]  References Cited
U.S. PATENT DOCUMENTS

| 3,950,333 | 4/1976 | Durant et al. | 424/273 R |
| 4,025,527 | 5/1977 | Durant et al. | 424/273 R |
| 4,118,502 | 10/1978 | Durant et al. | 424/273 R |
| 4,163,781 | 8/1979 | Cragoe et al. | 424/200 |

FOREIGN PATENT DOCUMENTS 852324 9/1977 Belgium .
2342982 9/1977 France .

*Primary Examiner*—Alan L. Rotman
*Assistant Examiner*—Natalia Harkaway
*Attorney, Agent, or Firm*—Joan S. Keps; Richard D. Foggio; Alan D. Lourie

[57]  ABSTRACT

Amidine phosphonates carrying an unsaturated nitrogen heterocycle-containing substituent, representative of which are N-methyl-N'-[2-(2-thiazolylmethylthio)ethyl]amidinophosphonic acid monoethyl ester and N'-methyl-N''-[2-((5-methyl-4-imidazolyl)-methylthio)ethyl]guanidinophosphonic acid monobenzyl ester, are histamine $H_2$-antagonists.

10 Claims, No Drawings

AMIDINO AND GUANIDINO PHOSPHONATES

This is a division of application Ser. No. 913,180 filed June 6, 1978, now U.S. Pat. No. 4,190,664.

This invention relates to amidine compounds, their preparation, to pharmaceutical compositions containing certain of them, and to methods of blocking histamine $H_2$-receptors by administering such compounds.

Many physiologically-active substances elicit their biological actions by interaction with specific sites known as receptors. Histamine is such a substance and has a number of biological actions. Those biological actions of histamine which are inhibited by drugs commonly called "antihistamines", of which mepyramine, diphenhydramine and chlorpheniramine are typical examples, are mediated through histamine $H_1$-receptors. However, others of the biological actions of histamine are not inhibited by "antihistamines" and actions of this type which are inhibited by burimamide are mediated through receptors which are termed histamine $H_2$-receptors, and which may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure.

The present invention provides an amidine phosphonate compound of Structure 1:

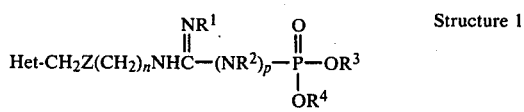

Structure 1 in which

Het is a 5- or 6-membered fully unsaturated heterocycle containing at least one nitrogen atom and optionally substituted by lower alkyl, trifluoromethyl, hydroxymethyl, halogen, hydroxy or lower alkoxy;

Z is a sulphur or methylene;

n is 2 or 3;

$R^1$ is hydrogen, lower alkyl or Het—$CH_2Z(CH_2)_n$—;

p is 0 or 1;

$R^2$ is hydrogen or lower alkyl;

or $R^1$ and $R^2$ together form a $(CH_2)_2$ or $(CH_2)_3$ group;

$R^3$ is lower alkyl, aryl or aryl(lower alkyl); and $R^4$ is hydrogen when p is 0 and hydrogen, lower alkyl, aryl or aryl(lower alkyl) when p is 1.

The above compounds where $R^4$ is hydrogen, which are phosphonic acid mono-esters, are the first phosphorus compounds to be discovered to be histamine $H_2$-antagonists, and the remaining compounds, namely those where p is 1 and $R^4$ is lower alkyl, aryl or aryl(lower alkyl), which are phosphonic acid diesters, are useful as intermediates for conversion by hydrolysis to the histamine $H_2$-antagonists where p is 1 and $R^4$ is hydrogen.

Structure 1 is representative of the tautomeric forms in which the compounds can exist. The compounds where $R^4$ is hydrogen (the mono-esters) have both basic and acidic character and can be prepared in the form of their acid addition salts or their salts with bases such as sodium hydroxide as well as in zwitterionic form. The compounds where $R^4$ is not hydrogen (the di-esters) have basic character and can be prepared in the form of their acid addition salts. The pharmaceutically-acceptable acid addition salts and salts with bases are particularly concerned.

In this specification by 'lower alkyl' and 'lower alkoxy' are meant an alkyl or alkoxy group having from 1 to 4 carbon atoms: it can be straight or branched. An aryl group is preferably phenyl.

Examples of heterocycles of the group Het are imidazole, pyridine, thiazole, isothiazole, oxazole, isoxazole, triazole and thiadiazole. Preferably the group Het is linked to $CH_2Z$ by a carbon atom of the heterocycle adjacent to a nitrogen atom. Preferably the heterocycle of Het is imidazole, particularly Het- is 2- or 4-imidazolyl optionally substituted by lower alkyl (especially methyl) hydroxymethyl, or halogen (especially chlorine or bromine). Especially valuable are compounds where Het- is a 5-methyl-4-imidazolyl or 2-thiazolyl group. Other suitable groups are 2-pyridyl optionally substituted by lower alkyl (especially methyl), halogen (especially chlorine or bromine), hydroxy or lower alkoxy (especially methoxy), 3-isothiazolyl optionally substituted by chlorine or bromine, 3-(1,2,5)-thiadiazolyl optionally substituted by chlorine or bromine and 2-(1,3,4-thiadiazolyl). Where R' is Het—$CH_2Z(CH_2)_n$—, this can be the same as or different from the Het—$CH_2Z(CH_2)_n$ shown in Structure 1.

Preferably Z is sulphur and n is 2. Where p is 1, preferably $R^2$ is hydrogen. Where $R^1$ is lower alkyl preferably it is methyl. Where $R^1$ and $R^2$ together form a $(CH_2)_2$ or $(CH_2)_3$ group, preferably they form a $(CH_2)_2$ group, which together with the adjacent nitrogen atoms and the carbon between them form an imidazoline ring. Particularly suitable compounds are those in which $R^3$ is methyl, ethyl, phenyl and benzyl.

Examples of phosphonic acids particularly suitable as the parent acids of the mono- and di-esters of Structure 1 are:

A. N'-methyl-N"-[2-((-5-methyl-4-imidazolyl)methylthio)ethyl]-amidinophosphonic acid, B. N'-methyl-N"-[2-(2-thiazolylmethylthio)ethyl]amidinophosphonic acid, C. N'-methyl-N"-[2-((5-methyl-4-imidazolyl)methylthio)ethyl]-guanidinophosphonic acid, and D. N,N'-ethylene-N"-[2-((5-methyl-4-imidazolyl)methylthio)ethyl]-guanidino-N-phosphonic acid.

Specific examples of intermediate di-esters of the invention are the dibenzyl and benzyl ethyl esters of the phosphonic acid C. Specific examples of the mono-esters of the invention, which are $H_2$-antagonists, are the methyl and ethyl esters of the phosphonic acid A, the ethyl ester of the phosphonic acid B, the ethyl and benzyl esters of the phosphonic acid C, and the benzyl ester of the phosphonic acid D.

In a process of the invention a compound of Structure 1 is prepared by reacting a primary amino compound $R^1NH_2$ or Het—$CH_2Z(CH_2)_nNH_2$ with the complementary compound of Structure 2 or 3

$$\text{Het-CH}_2\text{Z(CH}_2)_n\text{N}=\overset{\overset{\text{SA}}{|}}{\text{C}}-(\text{NR}^2)_p-\overset{\overset{\text{O}}{\|}}{\underset{\underset{\text{OR}^4}{|}}{\text{P}}}-\text{OR}^3 \quad \text{Structure 2}$$

$$\text{R}^1\text{N}=\overset{\overset{\text{SA}}{|}}{\text{C}}-(\text{NR}^2)_p-\overset{\overset{\text{O}}{\|}}{\underset{\underset{\text{OR}^4}{|}}{\text{P}}}-\text{OR}^3 \quad \text{Structure 3}$$

where A is lower alkyl, aryl or aryl(lower alkyl), (and Het, Z, n, $R^1$, $R^2$, $R^3$ and $R^4$ are as defined for Structure 1); provided that where p is O, $R^4$ is hydrogen; and where $R^4$ in the product is lower alkyl, aryl or aryl(lower alkyl) and a compound where $R^4$ is hydrogen is required, the product is selectively hydrolysed.

In accordance with the above, compounds where p is O are prepared by reaction of the appropriate primary amino compound with a phosphonic monoester of Structure 4 or 5.

$$\text{Het-CH}_2\text{Z(CH}_2)_n\text{N}=\overset{\overset{\text{SA}}{|}}{\underset{\underset{\text{OH}}{|}}{\text{C}}}-\overset{\overset{\text{O}}{\nearrow\!\!\!\!/}}{\text{P}}-\text{OR}^3 \quad \text{Structure 4}$$

$$\text{R}^1\text{N}=\overset{\overset{\text{SA}}{|}}{\underset{\underset{\text{OH}}{|}}{\text{C}}}-\overset{\overset{\text{O}}{\nearrow\!\!\!\!/}}{\text{P}}-\text{OR}^3 \quad \text{Structure 5}$$

These starting materials can be obtained by the reaction of an organic iodide AI, especially methyl iodide, with a corresponding intermediate compound Het—$CH_2Z(CH_2)_n$NHCSPO($OR^3$)($OR^4$) or $R^1$NHCSPO($OR^3$)($OR^4$), when the sulphur atom is alkylated and the group $R^4$ is removed. Intermediates of this type can themselves be prepared by the reaction of a compound $R^3OPX_2$ where X is chlorine with one equivalent of an alcohol $R^4$OH in the presence of a tertiary amine to form a compound XP($OR^3$)($OR^4$), followed by hydrolysis with water to a compound HPO($OR^3$)($OR^4$) and reaction of this with an isothiocyanate Het—$CH_2Z(CH_2)_n$NCS or $R^1$NCS, for instance using sodium methoxide in methanol. Preferably A is methyl: preferably X is chlorine.

The amidine phosphonate compounds of Structure 1 where p is 1 can be prepared by a process in which the units of the structure represented by Het—$CH_2Z(CH_2)_n$NH—, $R^1$N=, =$CNR^2$— and —PO($OR^3$)($OR^4$) (designated units 1a, 1b, 2 and 3 respectively) are brought together in the correct sequence using as reagents compounds of the following structure

| | |
|---|---|
| for unit 1a | Het-CH$_2$Z(CH$_2$)$_n$NH$_2$ |
| for unit 1b | R$^1$NH$_2$ |
| for unit 2 | (AS)$_2$C=NR$^2$ |
| for unit 3 | XPO(OR$^3$)(OR$^4$) | where X is halogen and each of $R^3$ and $R^4$ is lower alkyl, aryl or aryl(lower alkyl), with, if required, conversion of the group $R^4$ to hydrogen in the end-product. Preferably A is methyl: preferably X is chlorine.

Thus the unit 1a or 1b reagents can be coupled with the unit 2 reagent by known procedures to give respectively the unit combination 1a2 and 1b2 of Structures 6 and 7.

$$\text{Het-CH}_2\text{Z(CH}_2)_n\text{N}=\overset{\overset{\text{SA}}{|}}{\text{C}}\text{NHR}^2 \quad \text{Structure 6}$$

$$\text{R}^1\text{N}=\overset{\overset{\text{SA}}{|}}{\text{C}}\text{NHR}^2 \quad \text{Structure 7}$$

Alternatively the unit 2 reagent where $R^2$ is hydrogen can be coupled with the unit 3 reagent by known procedures to give the unit combination 23 of Structure 8

$$(\text{AS})_2\text{C}=\text{N}\overset{\overset{\text{O}}{\|}}{\underset{\underset{\text{OR}^4}{|}}{\text{P}}}-\text{OR}^3 \quad \text{Structure 8}$$

In the next step the unit combination 1a2 or 1b2 can be coupled with the unit 1b or 1a reagent, respectively, to give the unit combination 1ab2 of Structure 9

$$\text{Het-CH}_2\text{Z(CH}_2)_n\text{NH}\overset{\overset{\text{NR}^1}{\|}}{\text{C}}\text{NHR}^2 \quad \text{Structure 9}$$

which is then coupled with the unit 3 reagent to give the unit combination 1ab23, representing an amidine phosphonate of Structure 1 in which the group $R^4$ can be converted to hydrogen by hydrolysis.

Alternatively the unit combinations 1a2 and 1b2 can be coupled with the unit 3 reagent, or the unit combination 23 can be coupled with the unit reagent 1a or 1b, to give the unit combinations 1a23 and 1b23 and these can be further coupled with the unit 1b and 1a reagents respectively, before or after converting the group $R^4$ to hydrogen.

The hydrolytic replacement by hydrogen of the organic group $R^4$ derived from the unit 3 reagent can be effected at any stage subsequent to the coupling of that reagent. Where $R^1$ is itself Het—$CH_2Z(CH_2)_n$—, the unit 1a and 1b reagents are the same and two equivalents of the amine can be coupled with unit 2 reagent to replce the two groups AS successively and produce the unit combination 1ab2 in one combined stage.

Whether the coupling reactions are effected with introduction of the phosphonate group by means of the unit 3 reagent before or after either or both the amine radicals by means of the unit 1a and 1b reagents, the end result is the same, so that the various possible sequences are chemically equivalent. The unit 2 reagent has obvious chemical equivalents which can be employed instead, in that the groups SA can be replaced by lower alkoxy, aryloxy or methylsulphinyl groups. The use of obvious chemical equivalents is to be considered as within the scope of the claims of this specification.

Preferably in a process for preparing a compound of Structure 1 where p is 1, the process comprises the preliminary step of reacting a compound of Structure 6 or 7 with a compound XPO($OR^3$)($OR^4$) where X is halogen and each of $R^3$ and $R^4$ is lower alkyl, aryl or aryl(lower alkyl). The invention also provides a process for preparing a compound of Structure 1 where p is 1, in which the units of structure of the compound represented by Het—$CH_2Z(CH_2)_2$NH—, $R^1$N=, =$CNR^2$—, and —PO($OR^3$)($OR^4$) are brought together in the correct sequence using as reagents compounds of the structure Het—$CH_2Z(CH_2)_n$NH$_2$, $R^1$NH$_2$, (AS)$_2$C=NR$^2$, and XPO($OR^3$)($OR^4$) where X is halogen and $R^4$ is lower alkyl, aryl or aryl(lower alkyl).

Where in the compound of Structure 1 $R^1$ and $R^2$ together form a $(CH_2)_2$ or $(CH_2)_3$ group, there are no corresponding separate units of structure 1b and 2, but these are taken together as a single unit

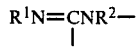

which is provided by the reagent $R^1NHC(SA)=NR^2$, and which is reacted with the unit 3 reagent described above, and then with the unit 1a reagent: or the compound of Structure 1 can be formed by the obvious chemical equivalent of using the reagents in the reverse order; and again the group $R^4$ can be converted to hydrogen at any time after coupling of the unit 3 reagent.

In a reagent of structure $XPO(OR^3)(OR^4)$, X is preferably chlorine. Such a reagent can be prepared by reacting a phosphoryl halide $POX_3$ with an equivalent amount of an alcohol $R^3OH$ or $R^4OH$ in the presence of an equivalent amount of a suitable base such as a tertiary amine, for instance triethylamine or pyridine: the second esterifying group is introduced into the product by displacement of a second halogen atom in the same way; or if $R^3$ and $R^4$ are the same, two equivalents of alcohol and base can be used to introduce both esterifying groups in one step. The unit reagents 1a, 1b and 2 can be prepared by known methods Coupling reactions using compounds in which the group SA is replaced by an amino (or imino) group in which the unit 3 reagent is employed can be carried out by known methods. In place of the unit 3 reagent there can be employed a compound of the same structure except that X is hydrogen, and reacting this in a two-phase system comprising aqueous sodium hydroxide and carbon tetrachloride with the appropriate compound containing the structural unit 2; an anion where X is replaced with a negative charge is initially formed and this reacts with carbon tetrachloride to give the chloro compound which is the unit 3 reagent.

The conversion of the group $R^4$ from lower alkyl, aryl or aryl(lower alkyl) to hydrogen can be effected by replacement under conditions which do not affect other groups present. When the conversion is effected on a compound in which all the structural units are present, the replacement can be effected by hydrolysis with an aqueous acid, for example hydrochloric or hydrobromic acid. Selective hydrolysis to replace $R^4$ but not $R^3$ as well is easy because removal of the second ester group is very difficult to effect. The groups $R^3$ and $R^4$ are so chosen that the desired group remains. A benzyl group is more readily cleaved with hydrobromic acid then a phenyl or ethyl group, so that compounds where $R^3$ is phenyl or ethyl and $R^4$ is hydrogen can be obtained by reaction of hydrobromic acid with the benzyl phenyl ester or the benzyl ether ester. The mono-ethyl ester can be obtained by reaction of the diethyl ester with sodium iodide in aqueous acetone. The monophenyl ester can be obtained from the diphenyl ester by reaction with sodium hydroxide under conditions sufficiently mild to avoid disruption of the remainder of the molecule. Where the conversion is effected on a compound containing an SA group (for example lower alkylthio), it can be carried out by treatment with aqueous pyridinium chloride or ammonium iodide.

The compounds of Structure 1 that are pharmacologically active are those in which $R^4$ is hydrogen. The active compounds block histamine $H_2$-receptors; that is, they inhibit the biological actions of histamine which are not inhibited by "antihistamines" such as mepyramine but are inhibited by burimamide. For example, they inhibit histamine-stumulated secretion of gastric acid from the lumen-perfused stomachs of rats anaesthetised with urethane, at doses of from 0.5 to 256 micromoles per kilogram intravenously. Their activity as histamine $H_2$-antagonists is also demonstrated by their ability to inhibit other actions of histamine which are not mediated by histamine $H_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously, they inhibit the vasodilator action of histamine. The potency of the compounds is illustrated by an effective dose producing 50% inhibition of gastric acid secretion in the anaesthetised rat and producing 50% inhibition of histamine-induced tachycardia in the isolated guinea pig atrium (less than $10^{-4}$ Molar).

The pharmaceutical compositions of the invention comprise a pharmaceutical carrier and a pharmacologically-active compound of the invention of Structure 1 where $R^4$ is hydrogen, which can be in the zwitterionic form or in the form of its addition salt with a pharmaceutically-acceptable acid or its salt with a pharmaceutically-acceptable base. Such acid addition salts include those with hydrochloric, hydrobromic, hydriodic, sulphuric and maleic acids and may conveniently be formed from the corresponding zwitterionic compounds by standard procedures, for example by treating them with an acid in a lower alkanol or by the use of ion exchange resins to form the required salt either directly or from a different addition salt. Salts with bases for example the sodium or potassium salts can be prepared in the usual way of neutralisation of the zwitterionic form.

The pharmaceutical carrier employed can be a solid or liquid. Examples of solid carriers are lactose, terra alba, sucrose, talc, gelatin, agar, pectin, acacia, magnesium stearate and stearic acid. Examples of liquid carriers are syrup, peanut oil, olive oil and water.

If a solid carrier is used, the composition can be prepared in the form of a tablet, capsule, troche or lozenge. The amount of solid carrier in a unit dosage form is generally from about 25 mg to about 300 mg. If a liquid carrier is used, the composition can be in the form of a syrup, emulsion, soft gelatin capsule, a sterile injectable liquid contained for example in an ampoule or an aqueous or non-aqueous liquid suspension. The pharmaceutical compositions are prepared by conventional techniques involving procedures such as mixing, granulating and compressing or dissolving the ingredients as appropriate to the desired preparation. The active ingredient is present in the compositions in an effective amount to block histamine $H_2$-receptors. Preferably, each dosage unit contains the active ingredient in an amount of from about 50 mg to about 250 mg.

The invention provides a method of blocking histamine $H_2$-receptors which comprises administering to an animal a pharmacologically-active compound of Structure 1 where $R^4$ is hydrogen, which can be in the zwitterionic form or in the form of its addition salt with a pharmaceutically-acceptable acid or its salt with a pharmaceutically-acceptable base, or a pharmaceutical composition containing the compound. The active ingredient will preferably be administered one to six times per day. The daily dosage regimen will generally be from about 150 mg to about 1500 mg. The route of administration may be oral or parenteral.

In the treatment of certain conditions, for example inflammation, and in inhibiting the actions of histamine on blood pressure, a combination of the histamine $H_2$-antagonists of the invention with histamine $H_1$-antagonists is useful.

The invention is illustrated by the following Examples in which temperatures are in °C.

EXAMPLE 1

Diethyl N-methylthiocarbamoylphosphonate, prepared according to K. A. Petrov and A. A. Neimysheva, Zhur. Obsch. Khimii, 1959, 29, 1819, was purified by chromatography on a silica gel column (eluant 20% ethyl acetate in light petroleum) to give yellow crystals, m.p. 50°–52°. This phosphonate (2.11 g, 0.01 mole) was dissolved in methyl iodide (10 ml), and the solution heated under reflux for 2 hours and then left at ambient temperature for a further 24 hours: N,S-dimethyl-thioimidoylphosphonic acid monoethyl ester crystallised out, and was recrystallised from acetonitrile, m.p. 142°–147° (dec).

The above ester (3.94 g, 0.02 mole) and 2-[(5-methyl-4-imidazolyl)]methylthio)ethylamine (3.42 g, 0.02 mole) were dissolved separately in 25 ml quantities of acetonitrile, and the solutions mixed. A thick oily layer appeared and after 30 minutes was separated off, diluted with methanol (4 ml) and extracted repeatedly with boiling acetone. The acetone fractions were combined and allowed to stand at ambient temperature for 18 hours, after which the product N-methyl-N'-[2-((5-methyl-4-imidazolyl)methylthio)ethyl]-amidinophosphonic acid monoethyl ester crystallised out m.p. 185°–187°, (Found: C, 40.7; H, 6.6; N, 17.1%. $C_{11}H_{21}N_4O_3PS$ requires: C, 41.2; H, 6.6; N, 17.5%).

EXAMPLE 2

Dimethyl N-methylthiocarbamoylphosphonate prepared by the method used for the diethyl ester (see Example 1) (1.8 g.) was dissolved in methyl iodide (10 ml) and the solution heated under reflux for 3 hours and kept at ambient temperature for 3 days under anhydrous conditions. N,S-dimethylthioimidoylphosphonic acid monomethyl ester crystallised out and this reagent (1.56 g) and 2-[(5-methyl-4-imidazolyl)-methylthio]ethylamine (1.36 g) in acetonitrile (50 ml), on standing at ambient temperature for 16 hours afforded N-methyl-N'-[2-((4-methyl-5-imidazolyl)methylthio)ethyl]-amidinophosphonic acid monomethyl ester, which was recrystallised from methanol-acetone, m.p. 170°–171°, (Found: C, 39.5; H, 6.5; N, 18.5%. $C_{10}H_{19}N_4O_3SP$ requires: C, 39.2; H, 6.3; N, 18.3%).

EXAMPLE 3

Reaction of dichlorophenoxyphosphine with an equivalent amount of benzyl alcohol in the presence of an equivalent amount of triethylamine and hydrolysis with water of the product yields benzyl phenyl phosphite. Reaction of this with methyl isothiocyanate gives benzyl phenyl N-methyl-thiocarbamoyl-phosphonate. When this is used instead of the corresponding diethyl compound in the procedure of Example 1, the monophenyl ester of N-methyl-N'-[2-((5-methyl-4-imidazolyl)methylthio)ethyl]amidinophosphonic acid is obtained.

EXAMPLE 4

Reaction of dibenzyl phosphite with methyl isothiocyanate gives dibenzyl N-methylthiocarbamoylphosphonate: use of this instead of the corresponding diethyl compound in the procedure of Example 1 gives the monobenzyl ester of N-methyl-N'-[2-((5-methyl-4-imidazolyl)methylthio)ethyl]-amidinophosphonic acid.

EXAMPLE 5

N,S-Dimethylthioimidoylphosphonic acid monoethyl ester (0.59 g) was added to a solution of 2-(2-thiazolylmethylthio)ethylamine dihydrobromide (1.0 g) in methanol (10 ml) containing triethylamine (0.61 g) and kept at ambient temperature for 24 hours. The reaction mixture was concentrated by evaporation and acetone added to precipitate triethylamine salt, which was removed by filtration; the filtrate was concentrated and purified on a silica gel column with elution initially by acetone-methanol (9:1) to remove impurities followed by acetone-methanol (1:1) to yield N-methyl-N'-[2-(2-thiazolylmethylthio)ethyl]amidinophosphonic acid monoethyl ester, which was recrystallised from methanol-ethyl acetate, m.p. 156°–158°, (Found: C,37.1; H, 5.6; N, 13.0%. $C_{10}H_{18}N_3O_3PS_2$ requires: C, 37.1; H, 5.4; N, 12.9%.

EXAMPLES 6 TO 15

When instead of 2-[(5-methyl-4-imidazolyl) methylthio]-ethylamine there is used in equivalent amounts in the process of Example 1 each of the following amines:

EXAMPLE 6. 2-[(4-imidazolyl)methylthio]ethylamine
7. 2-[(5-bromo-4-imidazolyl)methylthio]ethylamine
8. 2-[(3-chloro-2-pyridyl)methylthio]ethylamine
9. 2-[(3-methoxy-2-pyridyl)methylthio]ethylamine
10. 2-[(3-isothiazolyl)methylthio]ethylamine
11. 2-[(2-oxazolyl)methylthio]ethylamine
12. 2-[(3-1,2,4-triazolyl)methylthio]ethylamine
13. 2-[(2-1,3,4-thiadiazolyl)methylthio]ethylamine
14. 2-[(5-methyl-4-imidazolyl)methylthio]propylamine
15. 4-(4-imidazolyl)butylamine there are obtained the monoethyl esters of the corresponding N-methyl amidinophosphonic acids.

EXAMPLE 16

(a) N,S-Dimethyl isothiouronium iodide (23.2 g, 0.1 mole) was dissolved in water (40 ml), ice-cooled and vigorously stirred with a solution of dibenzylphosphite (26.2 g, 0.1 mole) in carbon tetrachloride (100 ml). Sodium hydroxide (8 g, 0.2 mole) dissolved in water (25 ml) was added during 30 minutes. After addition was complete the cooling bath was removed, and the stirring continued for a further 2 hours. The organic phase was separated, washed successively with dilute sulphuric acid, sodium bicarbonate solution and water, and dried over sodium sulphate. After removing the organic solvent the residue was chromatographed on a silica gel column, eluting with ethyl acetate-light petroleum 40°–60° (1:2) to give N,S-dimethyl-N'-(dibenzylphosphono)-isothiourea, m.p. 55°.

(b) To a stirred mixture of the isothiourea (3.65 g, 0.01 mole), 2-[(4-methyl-5-imidazolyl)methylthio]ethylamine (1.71 g, 0.01 mole) and 2 g. of Molecular Sieves 4A in 50 ml dry 2-propanol (2.32 g, 0.01 mole) was added silver oxide in several portions during 30 minutes. After 3 hours the reaction mixture was filtered and evaporated. The thick residue was chromatographed on a silica gel column, eluting with acetone containing 10% methanol, to give N'-methyl-N"-[2-((5-methyl-4-imidazolyl)methylthio)ethyl]guanidinophosphonic acid dibenzyl ester, (Found: C, 56.1; H, 6.3; N, 14.3%. $C_{23}H_{30}N_5O_3PS$ requires: C, 56.8; H, 6.0; N, 14.4%).

EXAMPLE 17

The guanidine obtained from the process of Example 16 (1.47 g, 0.003 mole) was dissolved in acetone (20 ml) and 48% aqueous hydrogen bromide (1:1 ml, 0.0064 mole) added. Methanol (2 ml) was added to prevent separation of phases and the solution kept for 18 hours, after which N'-methyl-N"-[2-((5-methyl-4-imidazolyl)methylthio)ethyl]guanidino-phosphonic acid monobenzyl ester hydrobromide had crystallised out, m.p. 146°–147°, (Found: C, 40.0; H, 5.3; N, 14.9; Br. 17.0%. $C_{16}H_{24}N_5O_3PS.HBr$ requires: C, 40.2; H, 5.3; N, 14.6; Br. 16.7%).

EXAMPLE 18

(a) While stirring and ice-cooling, a mixture of redistilled benzyl alcohol (10.8 g, 0.1 mole) and triethylamine (10.1 g, 0.1 mole) was added dropwise in 30 minutes to a solution of ethyldichlorophosphate ($C_2H_5OPOCl_2$)(16.3 g., 0.1 mole) in tetrahydrofuran (100 ml). After a further 2 hours of stirring at ambient temperature, the solution was filtered and almost all of the tetrahydrofuran removed at reduced pressure at 25° to give benzylethyl chlorophosphate as an oil. This was diluted with chloroform (80 ml) and cooled in an ice bath, a cold solution of N,S-dimethylisothiouronium iodide (23.2 g., 0.1 mole) in water (25 ml) was added and while vigorously stirring, a solution of sodium hydroxide (8 g., 0.2 mole) in water (15 ml) was added dropwise in 30 minutes. After addition was complete the cooling bath was removed, and vigorous stirring continued for a further 2 hours. The organic phase was then separated and treated by the same procedure as in Example (16a) to give N,S-dimethyl-N'-(benzylethylphosphono)isothiourea as an oil.

(b) Reaction of this isothiourea with 2-[(5-methyl-4-imidazolyl)methylthio]ethylamine using the procedure of Example 16(b) gave N'-methyl-N"-[2-((5-methyl-4-imidazolyl)-methylthio)ethyl]guanidinophosphonic acid benzyl ethyl ester.

EXAMPLE 19

The guanidine of Example 18 was hydrolysed with 48% aqueous hydrogen bromide using the procedure of Example 17 to give on recrystallisation from ethanol/ether N'-methyl-N"-[2-((5-methyl-4-imidazolyl)methylthio)ethyl]guanidinophosphonic acid monoethyl ester hydrobromide, 170°–172° C. (dec). (Found: C, 31.5; H, 5.6; N, 16.4; Br, 19.2%. $C_{11}H_{22}N_5O_3PS.HBr$. requires: C, 31.7; H, 5.6; N, 16.8; Br, 19.2%).

EXAMPLE 20

Use of phenyldichlorophosphate instead of ethyldichlorophosphate in the procedure of Example 18 gives N'-methyl-N"-[2-((5-methyl-4-imidazolyl)methylthio)ethyl]guanidinophosphonic acid benzylphenyl ester.

EXAMPLE 21

When the benzylphenyl ester obtained by the process of Example 20 is submitted to the procedure of Example 19 there is obtained N'-methyl-N"-[2-((5-methyl-4-imidazolyl)methylthio)ethyl]guanidinophosphoric acid monophenyl ester hydrobromide.

EXAMPLE 22 to 31

When instead of 2-[(4-methyl-5-imidazolyl)methylthio]-ethylamine there is used in the equivalent amounts in the process of Example 16(b) each of the following amines:

EXAMPLE 22. 2-[(4-imidazolyl)methylthio]ethylamine
23. 2-[(5-bromo-4-imidazolyl)methylthio]ethylamine
24. 2-[(3-chloro-2-pyridyl)methylthio]ethylamine
25. 2-[(3-methoxy-2-pyridyl)methylthio]ethylamine
26. 2-[(2-thiazolyl)methylthio]ethylamine
27. 2-[(3-isothiazolyl)methylthio]ethylamine
28. 2-[(2-oxazolyl)methylthio]ethylamine
29. 2-[(2-1,3,4-thiadiazolyl)methylthio]ethylamine
30. 2-[(3-1,2,4-triazolyl)methylthio]ethylamine
31. 4-(4-imidazolyl)butylamine there are obtained the dibenzyl esters of the corresponding guanidinophosphonic acids.

EXAMPLES 32 to 41

When the dibenzyl esters of Examples 22 to 31 are submitted to hydrolysis with 48% aqueous hydrogen bromide according to the procedure of Example 17 there are obtained respectively the hydrobromide salt of the monobenzyl ester of the following compounds:

EXAMPLE

32. N'-methyl-N"-[2-((4-imidazolyl)methylthio)ethyl]-guanidinophosphonic acid

EXAMPLE

33. N'-methyl-N"-[2-((5-bromo-4-imidazolyl)methylthio)ethyl]guanidinophosphonic acid
34. N'-methyl-N"-[2-((3-chloro-2-pyridyl)methylthio)ethyl]guanidinophosphonic acid
35. N'-methyl-N"-[2-((3-methoxy-2-pyridyl)methylthio)ethyl]guanidinophosphonic acid
36. N'-methyl-N"-[2-((2-thiazolyl)methylthio)ethyl]-guanidinophosphonic acid
37. N'-methyl-N"-[2-((3-isothiazolyl)methylthio)ethyl]-guanidinophosphonic acid
38. N'-methyl-N"-[2-((2-oxazolyl)methylthio)ethyl]-guanidinophosphonic acid
39. N'-methyl-N"-[2-((2-1,3,4-thiadiazolyl)methylthio)ethyl]-guanidinophosphonic acid
40. N'-methyl-N"-[2-((3-1,2,4-triazolyl)methylthio)ethyl]guanidinophosphonic acid
41. N'-methyl-N"-[4-(4-imidazolyl)butyl]guanidinophosphonic acid.

EXAMPLE 42

When S-methylisothiouronium iodide is used in equivalent amount instead of N,S-dimethylisothiouronium iodide in the process of Example 16, there is obtained as end-product N'-2-((5-methyl-4-imidazolyl)methylthio)ethyl]guanidinophosphonic acid dibenzyl ester.

EXAMPLE 43

When the di-ester obtained by the process of Example 42 is subjected to a hydrolysis similar to that described in Example 17, there is obtained N'-[2-((5-methyl-4-imidazolyl)-methylthio)ethyl]guanidinophosphonic acid monobenzyl ester.

EXAMPLE 44

When S-methyl-N-[2-((5-methyl-4-imidazolyl)methylthio)-ethyl]isothiouronium iodide is coupled with benzylethylchlorophosphate using the procedure of Example 18(a) there is obtained S-methyl-N-[2-((5-methyl-4-imidazolyl)methylthio)ethyl]-N'-(benzylethylphosphono)isothiourea. Reaction of this with 2-[(5-methyl-4-imidazolyl)methylthio]ethylamine by the procedure of Example 18(b) gives N',N''-bis-[2-((5-methyl-4-imidazolyl)methylthio)ethyl]guanidinophosphonic acid benzyl ethyl ester.

EXAMPLE 45

When the di-ester obtained by the process of Example 44 is subjected to a hydrolysis similar to that described in Example 17, there is obtained N',N''-bis-[2-((5-methyl-4-imidazolyl)methylthio)ethyl]guanidinophosphonic acid mon-ethyl ester.

EXAMPLE 46

When N,N'-S-trimethylisothiouronium iodide is coupled with benzylethylchlorophosphate using the procedure of Example 18(a) there is obtained N,N'-S-trimethyl-N'-(benzylethylphosphono)isothiourea. Reaction of this with 2-[(5-methyl-4-imidazolyl)methylthio]ethylamine by the procedure of Example 18(b) gives N,N'-dimethyl-N''-[2-((5-methyl-4-imidazolyl)methylthio)ethyl]guanidinophosphonic acid benzyl ethyl ester.

EXAMPLE 47

When the di-ester obtained by the process of Example 46 is subjected to a hydrolysis similar to that described in Example 17, there is obtained N,N'-dimethyl-N''-[2-((5-methyl-4-imidazolyl)methylthio)ethyl]-guanidinophosphonic acid mono-ethyl ester.

EXAMPLE 48

(a) Reaction of 2-methylthioimidazoline with dibenzylphosphite according to the procedure of Example 16(a) yields, as an oily liquid, N,N'-ethylene-N-(dibenzylphosphono)-S-methylisothiourea. The isothiourea (3.76 g) was dissolved in acetone (20 ml) and to the solution was added ammonium iodide (2.17 g) dissolved in methanol (8 ml). After 16 hours at ambient temperature N,N'-ethylene-S-methylisothiourea-N-phosphonic acid monobenzyl ester was separated as a hygroscopic oil by chromatography on a silica gel column using as eluant methanol/acetone (1:1).

(b) The isothiourea phosphonic ester (1.43 g) and 2-[5-methyl-4-imidazolyl)methylthio]ethylamine (0.86 g) were dissolved successively in propanol (10 ml). After standing at ambient temperature for 16 hours the product was isolated and purified by chromatography on a silica gel column using as eluant methanol/acetone (1:4), to give N,N'-ethylene-N''-[2-((5-methyl-4-imidazolyl)methylthio)ethyl]guanidinophosphonic acid monobenzyl ester, (Found: C, 48.4%, H, 5.9%, N, 15.8%. $C_{17}H_{24}N_5O_3PS.\frac{1}{2}H_2O$ requires: C, 48.8; H, 6.0; N, 16.8%): nmr:- (100 MHz. DMSO-$d_6$ $\delta$2.14 (s, $CH_3$-Imid), 2.65 (m, $CH_2CH_2S$), 3.40 (m, $NCH_2CH_2N$ and $NCH_2CH_2S$), 3.71 (s, Imid-$CH_2$), 4.79 (d, $CH_2OP$), 7.34 (s, benzylic $CH_2$), 7.48 (s, N=CH-N), 9.30 (broad, NH). All peaks had proper integrations.

EXAMPLE 49

A pharmaceutical composition is prepared from the following ingredients.

| | |
|---|---|
| N'-methyl-N''-[2-((5-methyl-4-imidazoly)methylthio)-ethyl]guanidinophosphonic acid monobenzyl ester hydrobromide | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 50

An injectable pharmaceutical composition is prepared by dissolving N'-methyl-N''-(2-(5-methyl-4-imidazolyl)methylthio)-ethylguanidinophosphonic acid monoethyl ester hydrobromide (100 g) in sterile water (2 liters). From it are prepared ampoules containing 100 mg of active ingredient.

EXAMPLE 51

A composition is prepared as in Example 49, but using as active ingredient N-methyl-N'-[2-(2-thiazolyl-methylthio)ethyl]amidinophosphonic acid monoethyl ester.

EXAMPLE 52

A composition is prepared as in Example 50, but using as active ingredient N-methyl-N'-[2-((5-methyl-4-imidazolyl)methylthio)ethyl]amidinophosphonic acid monoethyl ester as the hydrochloride salt.

Similarly other compounds of Structure 1 where $R^4$ is hydrogen can be formulated as pharmaceutical compositions by the procedures of Examples 49 to 52.

The pharmaceutical compositions prepared in the above Examples are administered to a subject within the dose range given above to block histamine $H_2$-receptors.

What is claimed is:

1. A compound of the structure

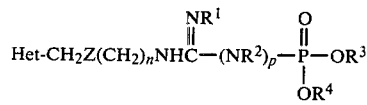

in which

Het is a 5- or 6-membered fully unsaturated heterocycle containing at least one nitrogen atom, said heterocycle being pyridine or triazole which is attached at a ring carbon, and optionally substituted by lower alkyl, trifluoromethyl, hydroxymethyl, halogen, hydroxy or lower alkoxy;

Z is sulphur or methylene;

n is 2 or 3, $R^1$ is hydrogen, lower alkyl or Het—$CH_2Z(CH_2)_n$—;

p is 0 or 1;

$R^2$ is hydrogen or lower alkyl;

or $R^1$ and $R^2$ together form a $(CH_2)_2$ or $(CH_2)_3$ group;

$R^3$ is lower alkyl, phenyl or phenyl(lower alkyl); and $R^4$ is hydrogen when p is 0 and hydrogen, lower alkyl, phenyl or phenyl(lower alkyl) when p is 1.

2. A compound according to claim 1, in which Het is linked to $CH_2Z$ by a carbon atom of the heterocycle adjacent to a nitrogen atom.

3. A compound according to claim 1, in which Z is sulphur and n is 2.

4. A compound according to claim 1, in which p is 1 and $R^2$ is hydrogen.

5. A compound according to claim 1, in which p is 0.

6. A compound according to claim 1, in which $R^1$ is methyl.

7. A compound according to claim 1, in which $R^1$ and $R^2$ together form a $(CH_2)_2$ group.

8. A compound according to claim 1, in which $R^4$ is hydrogen.

9. A pharmaceutical composition to block histamine $H_2$-receptors comprising in an effective amount to block said receptors a compound of claim 8 in combination with a pharmaceutically-acceptable diluent or carrier.

10. A method of blocking histamine $H_2$-receptors which comprises administering to an animal in an effective amount to block said receptors a compound of claim 8.

* * * * *